United States Patent
Abel

(10) Patent No.: US 10,034,726 B2
(45) Date of Patent: Jul. 31, 2018

(54) AIR ACTIVATED IMPRESSION SYRINGE TO DELIVER IMPRESSION MATERIAL AROUND TOOTH IN CROWN PREPARATION

(75) Inventor: Don E. Abel, Olney, IL (US)

(73) Assignee: DENTSPLY SIRONA Inc, York, PA (US)

(*) Notice: Subject to any disclaimer, the term of this patent is extended or adjusted under 35 U.S.C. 154(b) by 0 days.

(21) Appl. No.: 12/799,740

(22) Filed: Apr. 30, 2010

(65) Prior Publication Data

US 2010/0285425 A1 Nov. 11, 2010

Related U.S. Application Data

(60) Provisional application No. 61/175,515, filed on May 5, 2009.

(51) Int. Cl.
*A61C 3/02* (2006.01)
*A61C 9/00* (2006.01)

(52) U.S. Cl.
CPC .................. *A61C 9/0026* (2013.01)

(58) Field of Classification Search
CPC ......... A61C 5/062; A61C 5/064; A61C 5/068; A61C 5/066; A61C 19/06; A61C 19/26; B05C 17/00506
USPC ....... 433/80, 89, 90; 604/143; 222/372, 373, 222/389, 394–399
See application file for complete search history.

(56) References Cited

U.S. PATENT DOCUMENTS

| | | | | | |
|---|---|---|---|---|---|
| 3,827,147 | A | * | 8/1974 | Condon | 433/90 |
| 3,854,209 | A | * | 12/1974 | Franklin et al. | 433/90 |
| 4,693,684 | A | * | 9/1987 | Blatherwick et al. | 433/90 |
| 4,758,158 | A | * | 7/1988 | Pierce et al. | 433/90 |
| 4,768,954 | A | * | 9/1988 | Dragan | 433/90 |
| 4,784,607 | A | * | 11/1988 | Francois | 433/90 |
| 5,052,927 | A | * | 10/1991 | Discko, Jr. | A61C 5/66 433/90 |
| 5,286,257 | A | * | 2/1994 | Fischer | 604/82 |
| 5,324,273 | A | * | 6/1994 | Discko, Jr. | 604/240 |
| 5,707,234 | A | * | 1/1998 | Bender | 433/90 |
| 5,722,829 | A | * | 3/1998 | Wilcox et al. | 433/90 |
| 6,083,002 | A | * | 7/2000 | Martin et al. | 433/90 |
| 6,261,094 | B1 | * | 7/2001 | Dragan | 433/90 |
| 2006/0264838 | A1 | * | 11/2006 | Volckmann et al. | 604/209 |
| 2007/0068974 | A1 | * | 3/2007 | Tourigny | 222/389 |

* cited by examiner

*Primary Examiner* — Yogesh Patel
(74) *Attorney, Agent, or Firm* — Dentsply Sirona Inc.

(57) ABSTRACT

An air driven impression syringe designed to be held with a pen type grip and capable of precise placement of impression material. An embodiment of the device is a dental tool useful in the fabrication of dental prostheses capable of extruding impression material comprising a cylindrical grip body with two ends, an air-driven piston with a center rod; and
where the cylindrical body defines a bore to accept the air driven piston, a channel on one end of the syringe and a source of pressurized air. The syringe includes a disposable tip pre-loaded with dental impression material attached to the channel such that a second bore in said syringe tip containing dental impression material aligns with the rod and wherein the rod can extend beyond the end of the body into the second bore to extrude material from the tip.

7 Claims, 2 Drawing Sheets

AIR ACTIVATED IMPRESSION SYRINGE TO DELIVER IMPRESSION MATERIAL AROUND TOOTH IN CROWN PREPARATION

CROSS REFERENCES TO RELATED APPLICATIONS

U.S. Provisional Application for Patent No. 61/175,515, filed May 5, 2009, with title "Air Activated Impression Syringe to Deliver Impression Material Around Tooth in Crown Preparation" which is hereby incorporated by reference. Applicant claims priority pursuant to 35 U.S.C. Par. 119(e)(i).

STATEMENT AS TO RIGHTS TO INVENTIONS MADE UNDER FEDERALLY SPONSORED RESEARCH AND DEVELOPMENT

Not Applicable

BACKGROUND OF THE INVENTION

Field of the Invention

The present invention generally relates to dental instruments and, more specifically, to an air activated impression syringe used with a pen type grip designed to deliver impression material around a prepared tooth following crown preparation.

Current impression syringes include a pistol grip manual action that is very difficult to control when trying to grip with force to extrude impression material and keep the tip in a one or two millimeter sulcus. In the traditional technology impression materials of different viscosities (i.e., light bodied and heavy bodied) are used to take impressions. The traditional technology requires one or two cords placed around individual teeth to open the sulcus. In addition, air bubbles are a common source of impression failure.

As can be seen, there is a need for a pen type grip to maintain precise control while air pressure forces the impression material into the sulcus around the tooth.

SUMMARY OF THE INVENTION

One aspect of the present invention is an air driven impression syringe capable of precise placement of impression material including: a cylindrical body, a body end cap and an air driven piston with a center rod. The cylindrical body includes a bore to accept the air driven piston, a breech end loading design on one end and accepts the body end cap on the opposite end. The body end cap contains an air inlet fitting, The piston with the center rod moves freely within the bore of the body. Release of air pressure retracts the piston after air pressure is applied during operation.

These and other features, aspects and advantages of the present invention will become better understood with reference to the following drawings, description and claims.

DESCRIPTION OF THE PREFERRED EMBODIMENT

Figure 1:
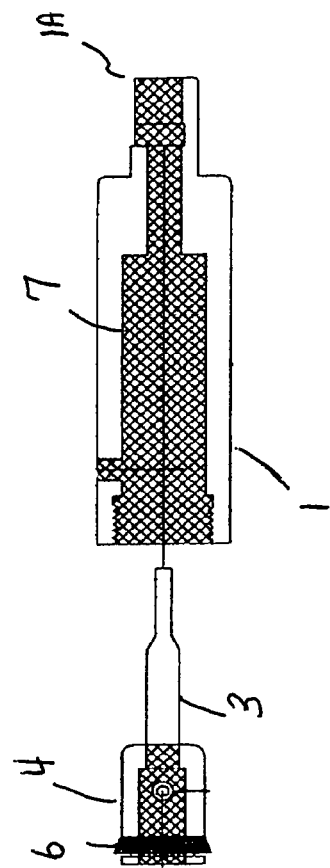
FIG. 1 depicts an exploded view of an exemplary embodiment of the device.
Figure 1:
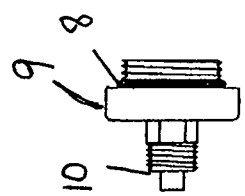

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, embodiments of the present invention generally provide a pneumatic impression syringe designed for use in the fabrication of dental prostheses. The pneumatic impression syringe utilizes external controlled air. The design allows a thumb and forefinger pen grasp. The pen grasp enables very precise placement of material into sulcus areas surrounding prepared teeth. The pneumatic impression syringe eliminates the use of a retraction cord to create a site for the impression material. The pneumatic impression syringe allows the use of a single impression material in place of the traditional two impression materials.

Elements of the device include a body 1 typically made of aluminum, a body end cap 9 typically made of aluminum, a piston 4 typically made of nylon with a center rod 3 typically made of steel. The cylindrical tool body 1 is designed with a bore 7 to accept the air driven piston 4. The piston 4 is sealed into the bore 7 of the body 1 via a rubber ring seal 6. The body 1 has a breech end loading design on one end and accepts the body end cap 9 on the opposite end. The body end cap 9 screws into the opposite end of the body 1 and is sealed by an O-ring 8. The body end cap 9 contains an air inlet fitting 10. The piston 4 with the center rod 3 moves freely within the bore 7 of the device body 1. Release of air pressure retracts the piston 4, and piston 4 retreats after air pressure is applied during operation.

One end 1A of the cylindrical body 1 is reduced in diameter. This end 1A has a breech-housing design to accommodate disposable plastic syringe tips preloaded with impression material. When air is applied, the piston 4 moves though the large end bore 7. The steel center rod 3 portion of this piston 4 moves through the small end of cylindrical body 1. When the piston rod 3 engages the preloaded syringe tip into the breech-loading area, impression material is extruded.

The pneumatic syringe procedure uses only one viscosity of impression material. The ability of the device to place the material into very small target areas (i.e., the sulcus) eliminates the necessity for the light bodied impression material. The heavy bodied material, when placed around prepared teeth, physically opens the sulcus.

Figure 2:
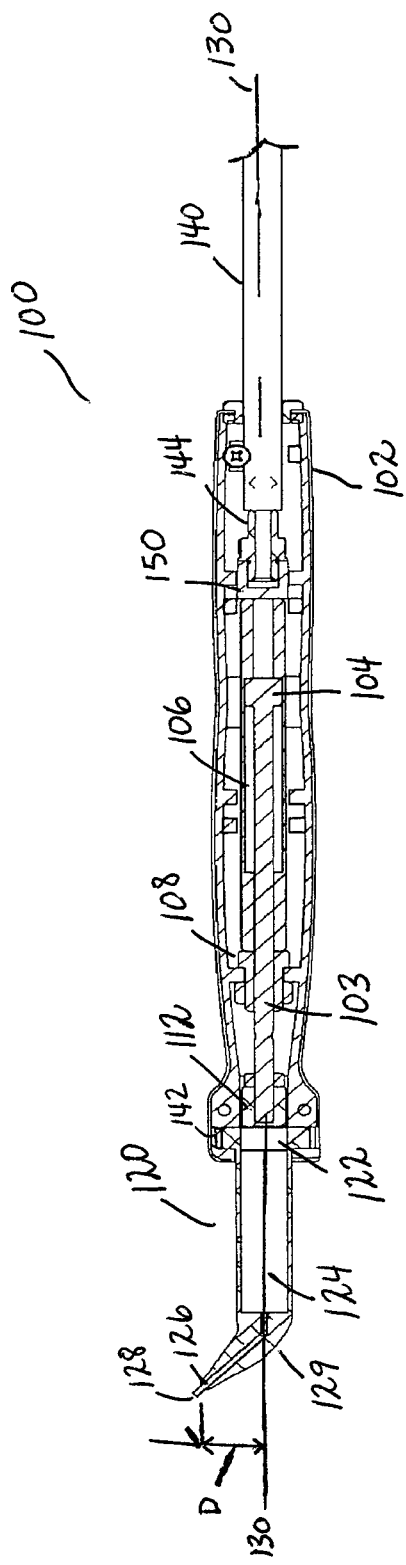
FIG. 2 depicts a cross sectional view of an alternate embodiment.

FIG. 2 shows a second embodiment of the pneumatic impression syringe 100. The syringe 100 includes a supply for pressurized air such as flexible hose 140 and air inlet fitting 144 and includes a body 102 typically made of aluminum. The body 102 is generally shaped as a long thin cylinder that can be gripped like a pen between the thumb and index finger. A piston 104 travels in a bore 106 and includes a center rod portion 103. The center rod 103 portion on the piston 104 engages a preloaded syringe tip 120, the tip 120 can be a disposable tip. The center rod 103 is guided by guide bearings 108 and can include a plunger 112 that engages a second piston 122 in the disposable syringe tip 120. The syringe tip 120 includes a bore 124 aligned with the plunger 112 and piston 104, the bore 124 is filled with paste impression material that can be extruded through channel 126 and out a small opening 128 in the end of the tip 120. The tip 120 includes a bent portion 129 that is bent at an angle of about 45 degrees. This displaces the channel 126 from the centerline 130 of the syringe 100 and places the opening 128 at a desired distance and angle from the centerline of the tool to allow effective placement of impression material in the sulcus. The syringe 100 can include a control such as finger tip control 150 or foot control (not shown) that controls the flow of material by controlling the flow of air from 140.

In use the syringe tip 120 can be slipped into a channel 142 on the end of the body 102 until the 124 aligns with the centerline of the syringe 100. Then by applying pressure to piston 104 the center rod 103 drives the plunger 112 into the bore 124 and impression material is then driven through channel 126 and out opening 128. As can be seen in FIG. 2 the opening 128 is displaced from the center line 130 by an angle of approximately 45 degrees and by a distance 'D' that will make the extrusion of material from said opening 128 easy to place in the sulcus and easy to see during the operation. When the plunger 112 drives the piston 122 to the end of the tip 120 the piston 104 can be retracted and the tip 120 can either be re-loaded with material or quickly replaced with a second tip such that the operation can continue before the material in the sulcus has a chance to begin to cure or harden.

It should be understood, of course, that the foregoing relates to exemplary embodiments of the invention and that modifications may be made without departing from the spirit and scope of the invention as set forth in the following claims.

I claim:

1. An air driven impression syringe comprising:
a cylindrical body with two ends;
an air driven piston with a center rod; and
wherein the cylindrical body has a first bore to accept the air driven piston, a breech end loading design on one end and a source of pressurized air, and wherein a body end opposite said breech end contains an air inlet fitting, the piston with the center rod moves freely within the first bore of the body, and a syringe tip containing dental impression material and is attached to said breech end such that a second bore in said syringe tip containing dental impression material aligns with said rod wherein said rod includes a plunger, a second piston bore in said second bore and wherein said center rod is contacted by at least one bearing spaced from said air driven piston, said at least one bearing having a body portion and a distal end, and wherein said distal end having a width greater than said body portion, and wherein said plunger and said center rod is guided by said at least one bearing and wherein said bearing defines a path for said center rod to travel, and said center rod can extend beyond the breech end of said body into said tip and wherein said plunger engages a second piston when said plunger enters said second bore and said plunger retracts from said second piston when the air driven piston retracts, and
wherein said air driven impression syringe has a pen type grip such that a user grips the air driven impression syringe between a thumb and index finger,
wherein said tip includes a channel to guide said dental impression material and includes an angled section wherein said angled section includes a tip opening displaced from a centerline of said cylindrical body and wherein said angled section of the tip and second bore of the tip are integrally connected,
wherein said tip is capable of fitting in a one or two millimeter sulcus and placing an impression material into said sulcus, and
wherein the air driven impression syringe includes a control that controls the flow of impression material into the sulcus.

2. The syringe of claim 1 wherein said tip is pre-loaded with dental impression material and is disposable.

3. A dental impression syringe comprising:
a cylindrical body with two ends;
a first piston with a center rod; and
wherein the cylindrical body has a first bore to accept the first piston, a breech end on one end and a source of pressurized air, and wherein a body end opposite said breech end contains an air inlet fitting, the piston with the center rod moves freely within the first bore of the body, and a tip containing dental impression material and is attached to said breech end such that a second bore in said syringe tip containing dental impression material aligns with said rod and wherein said center rod is contacted by a bearing spaced from said piston, said bearing having a body portion and a distal end, wherein said distal end having a width greater than said body portion, and wherein said bearing defines a path for said center rod to travel, and said center rod can extend beyond the end opposite said breech end of said body into said second bore wherein said rod includes a plunger, a second piston in said second bore of said tip and wherein said plunger engages said second piston when said plunger enters said second bore and said plunger retracts from said second piston when the air driven piston retracts, and
wherein said dental impression syringe has a pen type grip such that a user grips the air driven impression syringe between a thumb and index finger,
wherein said tip includes a channel to guide said dental impression material and includes an angled section wherein said angled section includes a tip opening displaced from a centerline of said cylindrical body by an angle such that material from said second bore is extruded from said tip opening and wherein said angled section of the tip and second bore of the tip are integrally connected,
wherein said tip is capable of fitting in a one or two millimeter sulcus and placing an impression material into said sulcus, and
wherein the air driven impression syringe includes a control that controls the flow of impression material into the sulcus.

4. The syringe of claim 3 wherein said first piston is air-driven.

5. The syringe of claim 3, wherein said tip is pre-loaded with dental impression material and is disposable.

6. A dental impression syringe comprising:
a cylindrical grip body with two ends;
a first piston with a center rod; and
wherein the cylindrical grip body has a first bore to accept the first air driven piston, a channel on one end and a source of pressurized air, and wherein a first body end contains an air inlet fitting, the piston with the center rod moves freely within the first bore of the body, and a tip containing dental impression material attached to said channel such that a second bore in said syringe tip containing dental impression material aligns with said rod and wherein said center rod is contacted by a bearing spaced from said piston, said bearing having a body portion and a distal end, wherein said distal end having a width greater than said body portion, and wherein said bearing defines a path that said center rod travels, and said center rod can extend beyond a second end of said body into said second bore to extrude material from said tip wherein said rod includes a plunger, a second piston in said second bore of said tip, and wherein said plunger engages said second piston when said plunger enters said second bore and said plunger retracts from said second piston when the air driven piston retracts, and wherein said dental impression syringe has a pen type grip such that a user grips the air driven impression syringe between a thumb and index finger, wherein said tip includes a channel to guide said dental impression material and includes an angled section wherein said angled section includes a tip opening displaced from a centerline of said cylindrical body such that material from said second bore is extruded from said tip opening wherein the tip opening is displaced from said centerline by a 45 degree angle and by a distance, and wherein said angled section of the tip and second bore of the tip are integrally connected.

wherein said tip is capable of fitting in a one or two millimeter sulcus and placing an impression material into said sulcus, and wherein the air driven impression syringe includes a control that controls the flow of impression material into the sulcus.

7. The syringe of claim 6, wherein said tip filled with dental impression material and is disposable.

* * * * *